(12) United States Patent
Lesser et al.

(10) Patent No.: US 10,207,097 B2
(45) Date of Patent: Feb. 19, 2019

(54) TAMPER-PROOF CONNECTOR/ADAPTER DEVICES AND RELATED METHODS

(71) Applicant: Smiths Medical ASD, Inc., Plymouth, MN (US)

(72) Inventors: Joseph Lesser, Minneapolis, MN (US); Mark Darst Rice, Minneapolis, MN (US); Sameer Mangal, St. Paul, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 151 days.

(21) Appl. No.: 15/133,968

(22) Filed: Apr. 20, 2016

(65) Prior Publication Data

US 2016/0310721 A1 Oct. 27, 2016

Related U.S. Application Data

(60) Provisional application No. 62/151,489, filed on Apr. 23, 2015.

(51) Int. Cl.
*A61M 39/10* (2006.01)
*A61M 5/00* (2006.01)
(Continued)

(52) U.S. Cl.
CPC .......... *A61M 39/1011* (2013.01); *A61M 5/00* (2013.01); *A61M 5/3216* (2013.01);
(Continued)

(58) Field of Classification Search
CPC .. A61M 39/00; A61M 39/10; A61M 39/1011; A61M 2039/1016; A61M 2039/1033; A61M 39/1055; A61M 2039/1066; A61M 2039/1077; A61M 39/165; A61M 39/20; A61M 2039/1094;
(Continued)

(56) References Cited

U.S. PATENT DOCUMENTS

| | | | |
|---|---|---|---|
| 4,895,570 A | | 1/1990 | Larkin |
| 4,909,794 A | * | 3/1990 | Haber ..................... A61M 5/24 604/110 |

(Continued)

FOREIGN PATENT DOCUMENTS

| | | |
|---|---|---|
| EP | 2545957 A1 | 1/2013 |
| WO | WO2008086631 | 7/2008 |

(Continued)

OTHER PUBLICATIONS

Small-bore connectors for liquids and gases in healthcare applications—Part 6: Connectors for neuraxial applications, ISO/IEC DIS 80369-6. Date: Nov. 18, 2013.

(Continued)

*Primary Examiner* — Bhisma Mehta
*Assistant Examiner* — William Frehe
(74) *Attorney, Agent, or Firm* — Patterson Thuente Pedersen, P.A.

(57) ABSTRACT

Embodiments of a tamper-proof adapter can be configured to provide interconnection of medical tubing or other devices with varying fitting or coupling types. In one embodiment, the adapter can permanently couple a first male Luer fitting to a second male ISO 80639-6 compliant fitting.

16 Claims, 12 Drawing Sheets

(51) Int. Cl.
*A61M 5/32* (2006.01)
*A61M 39/12* (2006.01)

(52) U.S. Cl.
CPC ..... *A61M 39/12* (2013.01); *A61M 2039/1066* (2013.01); *A61M 2039/1077* (2013.01); *A61M 2207/00* (2013.01)

(58) Field of Classification Search
CPC ............ A61M 39/12; A61M 2209/045; A61M 2205/6045; A61M 2005/247; A61M 2005/2474; A61M 2039/1083; H01R 13/59; H01R 13/62; H01R 13/629; A61B 2562/225; A61B 2018/00172
See application file for complete search history.

(56) References Cited

U.S. PATENT DOCUMENTS

| | | | | |
|---|---|---|---|---|
| 5,609,195 | A * | 3/1997 | Stricklin | F16L 37/28 137/614.04 |
| 7,678,101 | B2 | 3/2010 | Sage | |
| 8,721,628 | B2 | 5/2014 | Ziman | |
| 8,997,746 | B2 | 4/2015 | Matlock et al. | |
| 2002/0032436 | A1 * | 3/2002 | Mogg | A61M 39/0613 606/1 |
| 2005/0209581 | A1 | 9/2005 | Butts et al. | |
| 2005/0225082 | A1 * | 10/2005 | Dalle | A61M 39/1011 285/330 |
| 2010/0016838 | A1 * | 1/2010 | Butts | A61M 25/0097 604/535 |
| 2012/0041426 | A1 * | 2/2012 | Bizup | A61M 39/1011 604/536 |
| 2012/0245564 | A1 * | 9/2012 | Tekeste | A61M 5/3134 604/535 |

FOREIGN PATENT DOCUMENTS

WO   WO 2011/150037 A1   12/2011
WO   WO 2014/131981 A1   9/2014

OTHER PUBLICATIONS

International Search Report and Written Opinion for International Application No. PCT/US2016/025488 dated Jul. 12, 2016.
Search Report dated Oct. 4, 2018 for EP Application No. 16783570.1, 9 pages.

* cited by examiner

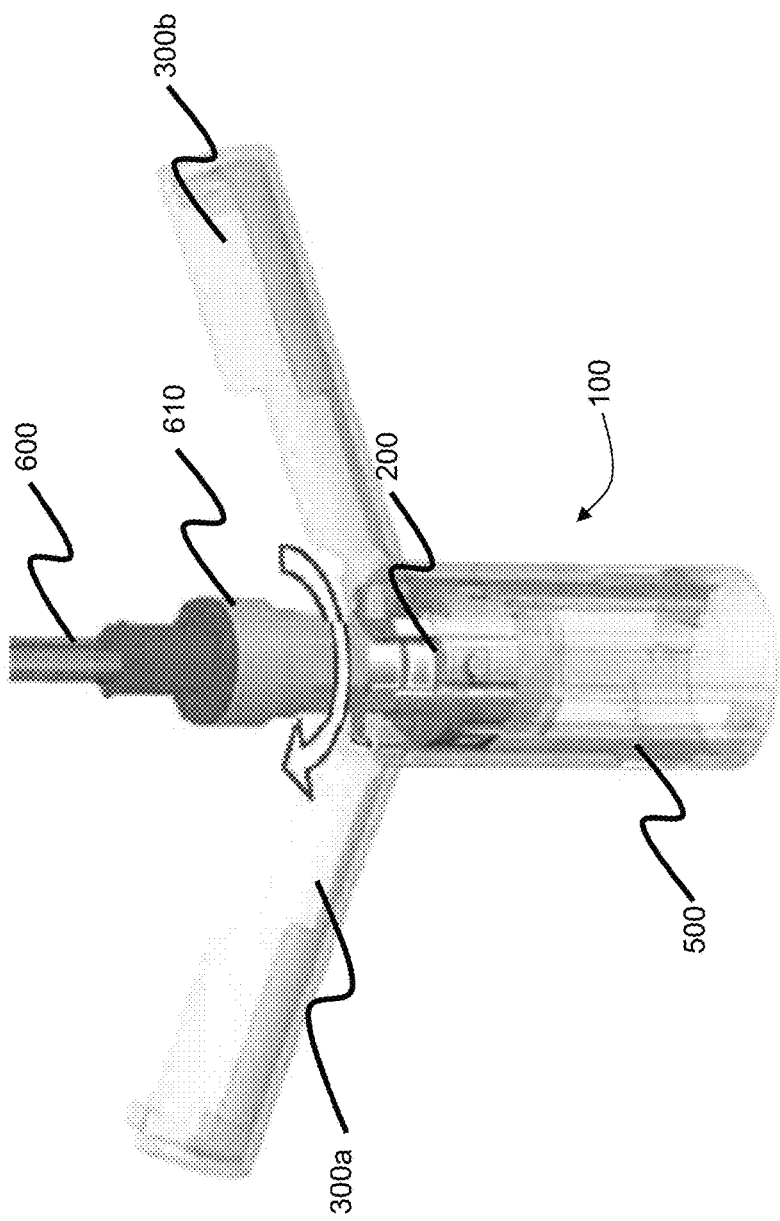

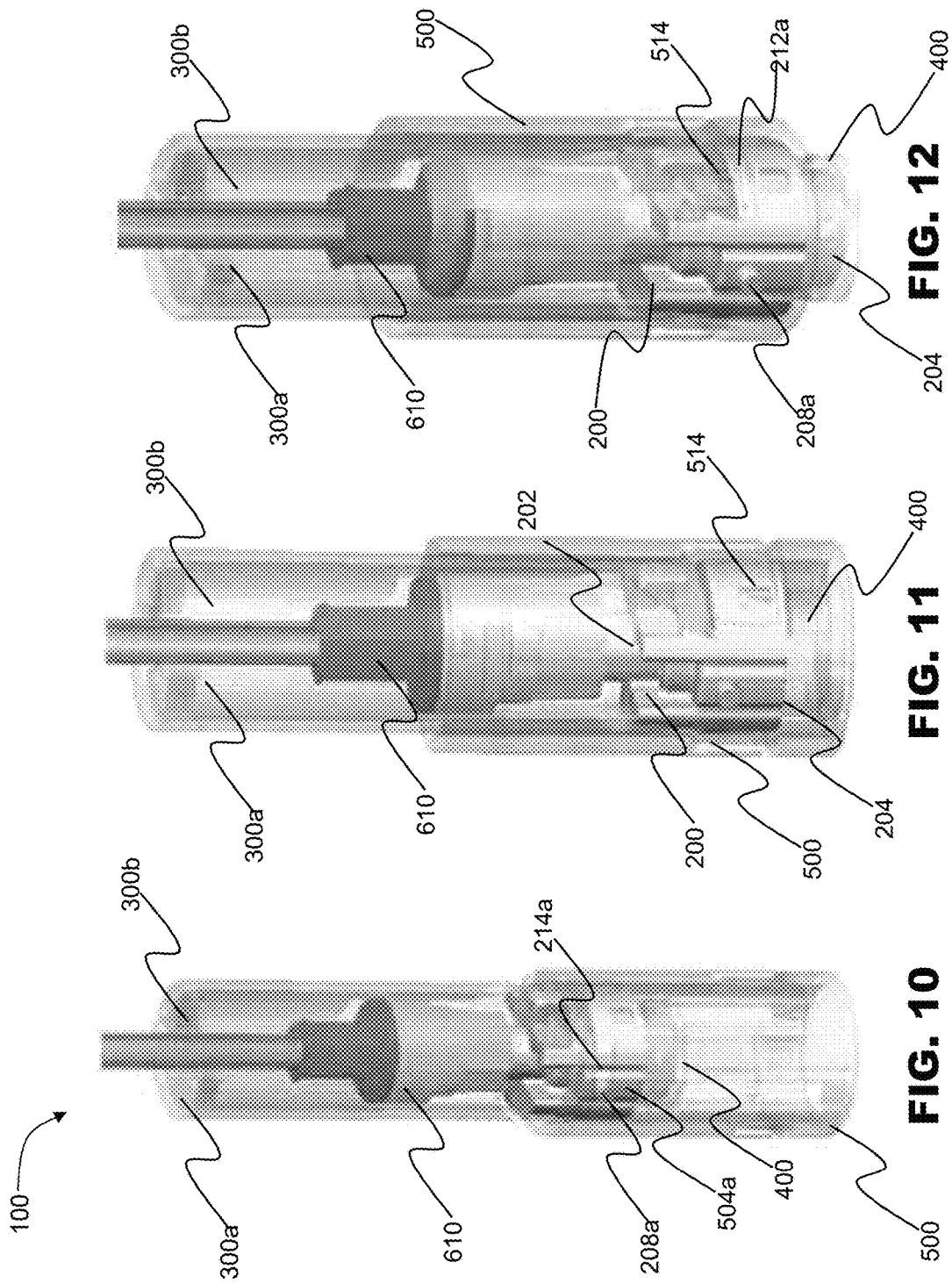

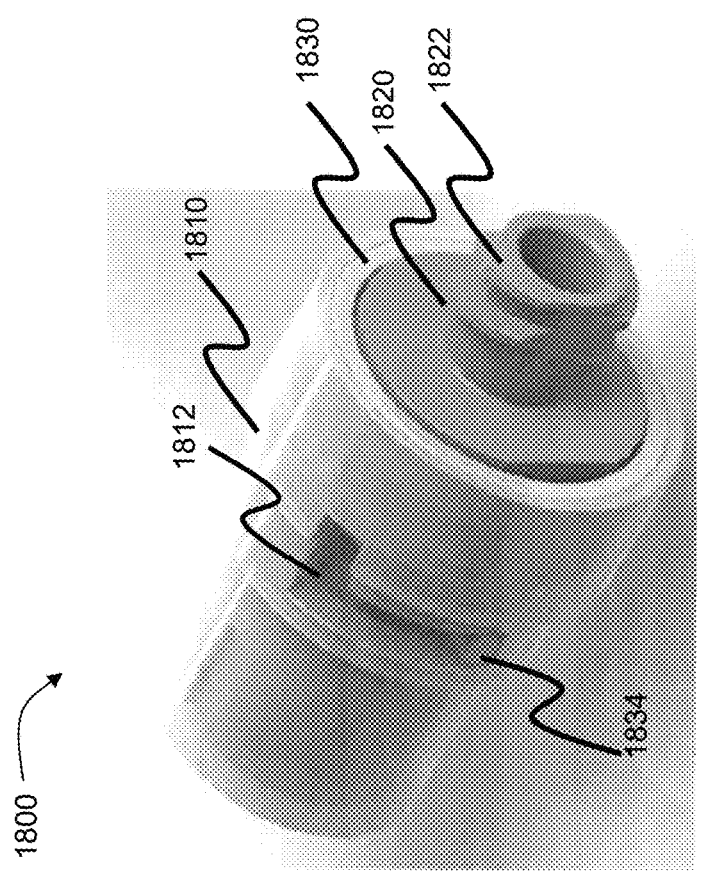

TAMPER-PROOF CONNECTOR/ADAPTER DEVICES AND RELATED METHODS

RELATED APPLICATION

The present application claims the benefit of U.S. Provisional Application No. 62/151,489 filed Apr. 23, 2015, which is hereby incorporated herein in its entirety by reference.

TECHNICAL FIELD

Embodiments relate generally to medical connectors through which fluids flow, and more particularly to medical connectors that are also adapters between diverse tubing and fitting types.

BACKGROUND

Infusion pumps are used to administer various types of drugs, nutritional compositions, and prescribed fluids or fluid-like substances (collectively, "medicaments") to patients in volume- and/or time-controlled doses. The pumps can be used to transfer medicaments, that are stored in storage containers such as cassettes and bags, to be administered to patients via infusion systems through various routes of delivery, such as intravenously, neuraxially, and enterally. Of necessity, the infusion systems typically include various conduits and connectors for connecting the storage containers to the pumps, and the pumps to patients.

Luer connectors are commonly used to make leak-free connections between medicament containers, conduits, pumps and patients. A Luer male-taper fitting can quickly and effectively be inserted into a corresponding female part to effect a reliable fluid tight connection. Notwithstanding the effectiveness and ease of use provided by Luer connectors, concern has grown regarding the widespread use of a single type of connector in multiple applications that can be inherently incompatible. In particular, the use of a single type of connector invites the possibility of misconnecting a fluid source to an incompatible route of delivery. A medicament to be delivered enterally through a percutaneous endoscopic gastrostomy PEG tube, for example, could mistakenly be administered intravenously by misconnection to a peripheral cannula, if both the PEG tube and the cannula were fitted with the same type of connector. Even the same type of medicament will have different dosages depending on the route of delivery; and misapplication of either the medicament or the dosage through an inappropriate route of delivery can negate the curative benefit of the drug, and can, in some circumstances, even be fatal.

In an effort to reduce the potential for a misconnection leading to the introduction of a particular medicament via an undesired route of delivery or other error in dosage or administration, some health care facilities will mandate the use of certain pumps for certain routes of delivery or other such dedicated protocols in their health care facilities. For example, a particular brand and model of pump could be exclusively designated for use in neuraxial delivery applications. Users within a particular facility could be trained to recognize the particular brand and model of pump as being exclusively dedicated to the designated route, thereby reducing the chance of a wrong route administration for a particular patient. Such ad hoc efforts, however, do not provide the benefits of a universal standard; instead, these ad hoc efforts tend to artificially restrict the use of the health care facility's inventory of pumps while not necessarily restricting access as desired to improper delivery routes and the like.

ISO 80369, Small-bore Connectors for Liquids and Gases in Healthcare Applications (incorporated herein by reference in its entirety), is an emerging International Standard for connectivity between medical devices, patients, and accessories. Part 1 of ISO 80369, General Requirements (incorporated herein by reference in its entirety), was published in 2010, and Parts 2-7, addressing particular applications, are works in progress at the time of this disclosure. The ISO 80369 standard assigns specific connectors to specific routes of delivery, and makes those specific connectors exclusive to their designated route. Segregating medicaments by route of delivery, and designating unique connectors for the different routes of delivery, is intended to reduce the opportunity for administration of a particular medicine via an inappropriate route of delivery.

The primary routes of delivery for medicament infusion systems are intravenous (IV), neuraxial, and enteral. Examples of infusion pumps used in medicament infusion systems include so called ambulatory pumps such as those sold by the assignee of the instant invention under the trade names CADD™ Prizm, Cadd™ Legacy, and CADD™ Solis. Such pumps are multipurpose pumps in that each can be used with an IV, neuraxial or enteral route of delivery, as well as others, by simply programming the individual pump appropriately. It will be understood that although this disclosure refers to and presents examples of particular pumps, embodiments applicable to any pump intended for administering medicaments such as syringe pumps, large volume pumps, elastomeric pumps and the like, while still other embodiments are applicable to devices and situations other than those involving or relating to medical pumps (e.g., using gravity-fed bags, in non-medical uses, etc.). On the other hand, ISO 80369, as a connectivity standard, segregates the connectors to be used for those three routes into separate categories, the connectors for each category being incompatible with, and unconnectable to, connectors from the other categories. While a multipurpose infusion pump can be used in different applications and for different delivery routes, the function of the pump needs to match, and needs to be restricted to, the delivery route it is assigned to, as do the connectors that incorporate the multipurpose pump into the infusion system, if the benefits of a connectivity standard are to be realized.

Conversion from Luer connectors to fully ISO 80369-compliant connectors will be a gradual process. For example, clinics will likely have a mix of Luer and neuraxial ISO 80369-6 devices that need to interconnect. Adapters are required that allow Luer connectors to attach to other ISO 80369 compliant devices. In the spirit of the ISO 80369 standard, it is desirable to provide a permanent, tamper-proof conversion from Luer connectors to other compliant devices.

SUMMARY

The challenges and needs outlined above are in large measure solved by embodiments of the adapters disclosed herein. In embodiments, the adapters provide a permanent, a tamper-proof conversion from one fitting type to another.

In an embodiment, an adapter comprises a connector comprising a first fitting arranged at a first end of the connector and a second fitting arranged at a second end of the connector, the first fitting configured to accept a first coupling and the second fitting configured to accept a second coupling, the second coupling being different from the first coupling; a shroud having a first end and a second end; and at least one wing moveably connected to the connector and configured to be closeable around the first fitting and the first coupling such that the wing and the connector can be moved within the shroud from the first end of the shroud toward the second end of the shroud to a locked position in which the first fitting and the first coupling are substantially enclosed within the shroud and the second fitting is at least partially exposed at the second end of the shroud.

In an embodiment, an adapter comprises a connector comprising a first fitting arranged at a first end of the connector and a second fitting arranged at a second end of the connector, the first fitting configured to accept a first coupling and the second fitting configured to accept a second coupling; a shroud having a first end and a second end; and a first wing and a second wing each moveably connected to the connector and configured to form a cylinder substantially enclosing the first fitting and the first coupling such that the cylinder and the connector can be moved within the shroud from the first end of the shroud toward the second end of the shroud to a locked position in which the first fitting is enclosed within the shroud and the second fitting is at least partially exposed at the second end of the shroud.

In an embodiment, a method comprises providing a connector comprising a first fitting at a first end of the connector and a second fitting at a second end of the connector, the first fitting configured to accept a first coupling and the second fitting configured to accept a second coupling; moveably coupling a first wing and a second wing to the connector such that the first and second wings can be selectively moved together to form a cylinder substantially enclosing the first fitting and the first coupling; and slidably coupling a shroud having a first end and a second end to the connector such that the second fitting is arranged substantially within the shroud, and the cylinder and the connector can be slid together within the shroud from a first end of the shroud toward the second end of the shroud to a locked position in which the first fitting and the first coupling are substantially enclosed within the cylinder and the shroud and the second fitting is substantially exposed at the second end of the shroud.

In an embodiment, an adapter comprises a connector comprising a first fitting and a second fitting configured to accept a first coupling and a second coupling, respectively, the first fitting being at a first end and of the connector and the second fitting being at a second end of the connector; one or more wings coupled to the connector and configured to be closeable to form a cylinder around the first fitting and the first coupling; a first shroud having a first end and a second end and an inner diameter sized to allow the connector and the cylinder to slide and rotate therewithin; and a second shroud coupled at a first end to the second end of the first shroud and having an inner diameter sized to allow the connector to slide and rotate therewithin, such that as the cylinder is advanced from the first end of the first shroud toward the second end of the first shroud, the connector rotates within the second shroud and moves toward the second end of the second shroud to a locked position in which the connector is prevented from movement toward the first end of the first shroud, the first fitting is enclosed within the first shroud, and the second fitting is at least partially exposed at the second end of the second shroud.

The above summary is not necessarily intended to describe each illustrated embodiment or every implementation of the subject matter hereof. The figures and the detailed description that follow more particularly exemplify these embodiments.

BRIEF DESCRIPTION OF THE DRAWINGS

Subject matter hereof may be more completely understood in consideration of the following detailed description of various embodiments of the subject matter in connection with the accompanying drawings, in which:

FIG. 9 is a perspective view of an assembled adapter according to an embodiment.

FIG. 10 is a perspective view of an adapter in an open mode according to an embodiment.

FIG. 11 is a perspective view of an adapter in a partially locked mode according to an embodiment.

FIG. 12 is a perspective view of an adapter in a locked mode according to an embodiment.

FIG. 16 is a perspective view of a cap of an adapter according to an embodiment.

Figure 1:
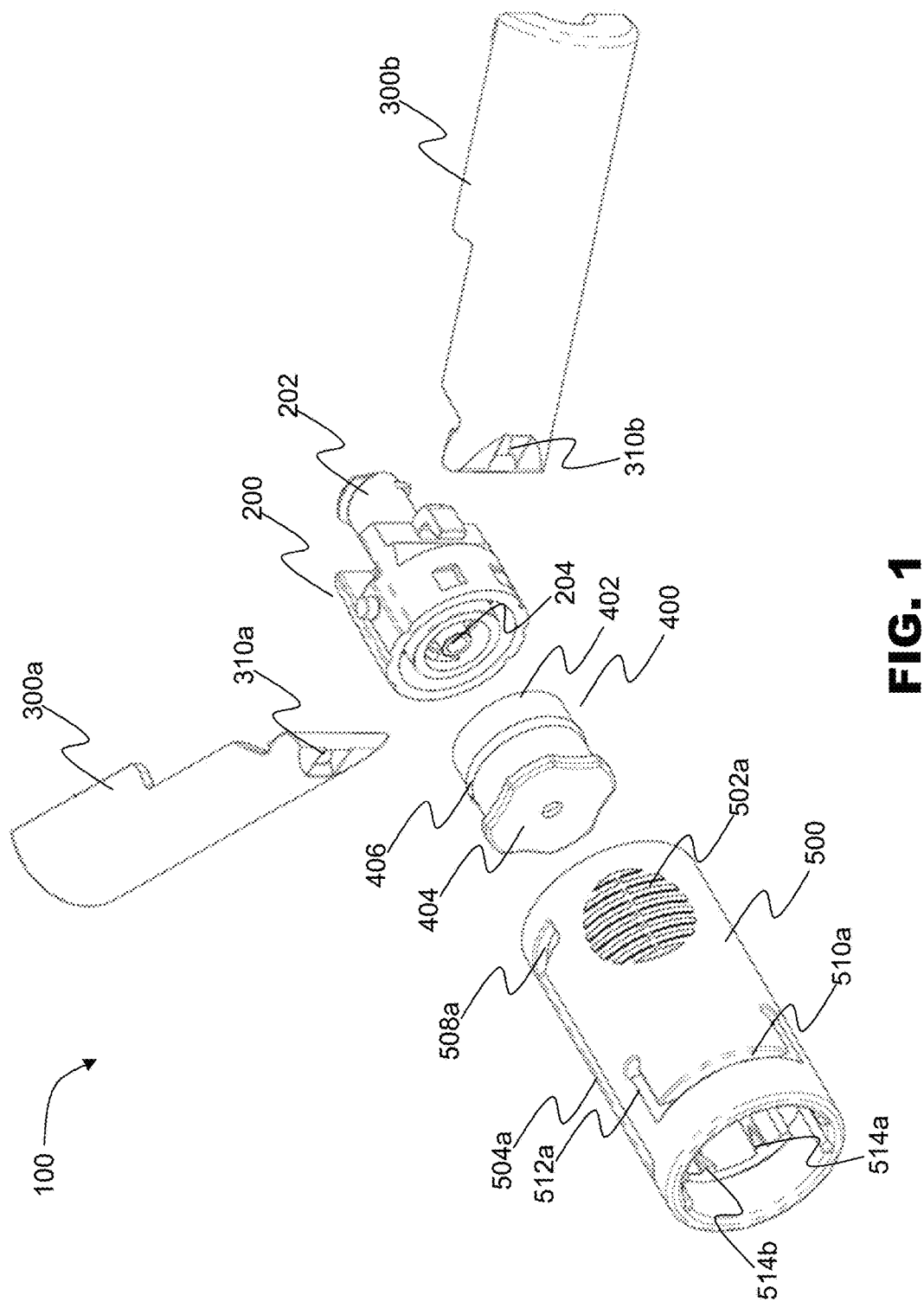
FIG. 1 is an exploded perspective view of the parts of an adapter according to an embodiment.

While embodiments are amenable to various modifications and alternative forms, specifics thereof have been shown by way of example in the drawings and will be described in detail. It should be understood, however, that the intention is not to limit subject matter hereof to the particular embodiments described. On the contrary, the intention is to cover all modifications, equivalents, and alternatives falling within the spirit and scope of subject matter hereof in accordance with the appended claims.

DETAILED DESCRIPTION

According to one embodiment, and as depicted in FIG. 1, an adapter 100 comprises a connector 200, wings 300a and 300b, a cap 400 and a shroud 500. Connector 200 can present first fitting 202 and second fitting 204 configured to enable a first coupling and a second coupling to be coupled thereto, respectively. In one example, adapter 100, via connector 200 with first fitting 202 and second fitting 204, enables an external male coupling of one type to connect to an external female coupling of another type, or vice versa, when each is coupled to adapter 100.

In the illustrated embodiment, first fitting 202 can be a female fitting, such as a Luer fitting in one example embodiment, and second fitting 204 can be a male fitting, such as a male ISO 80369-6 fitting in the example embodiment, enabling a male Luer fitting to connect to a female ISO 80369-6 fitting. Fittings 202 and 204 can, however, have different configurations in other embodiments allowing the interconnection of other fitting or coupling types, sizes, uses and the like. For example, the gender of fittings 202 and/or 204 can be reversed in other embodiments.

Figure 2:
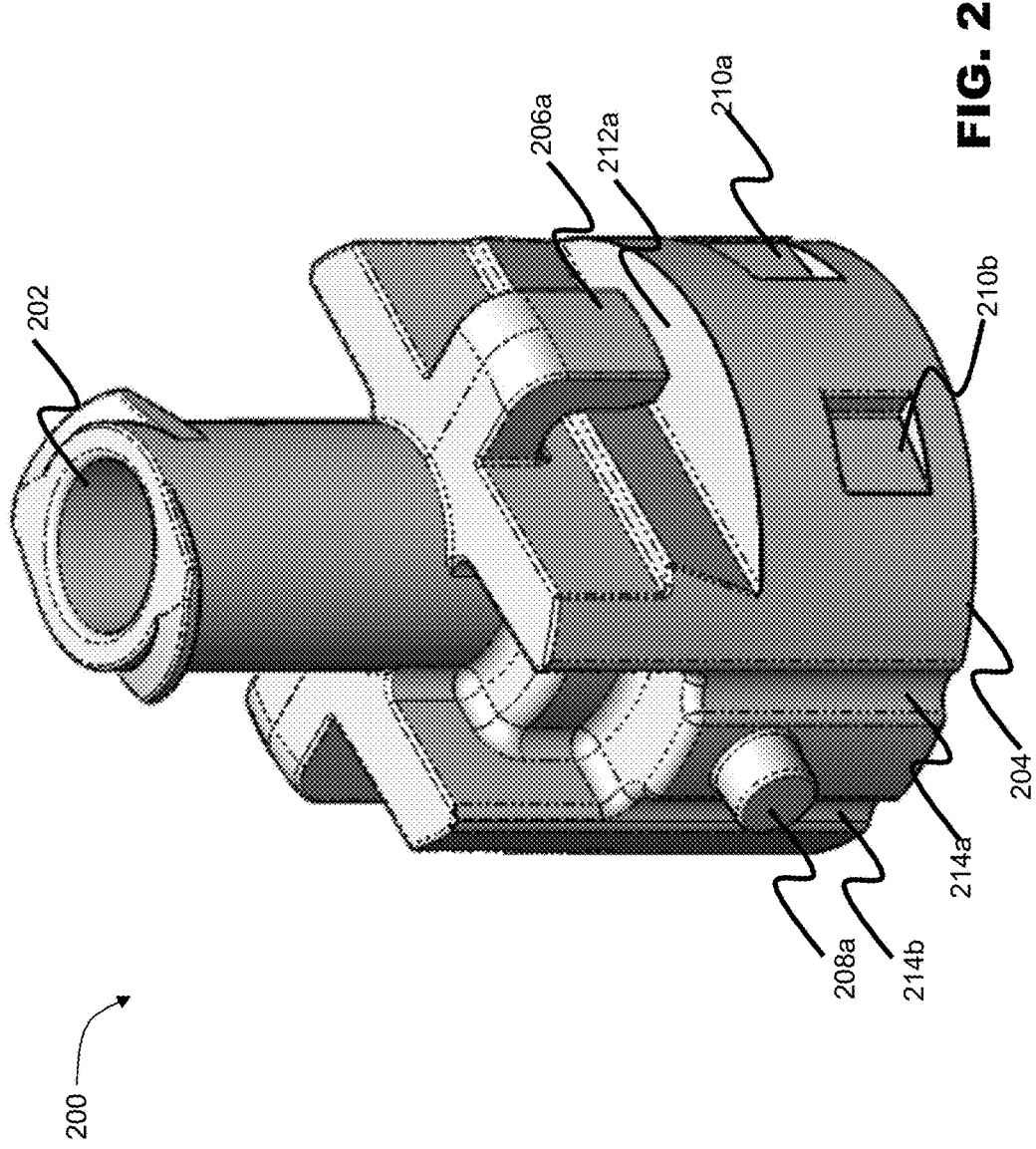
FIG. 2 is a perspective view of a connector of an adapter according to an embodiment.
Figure 3:
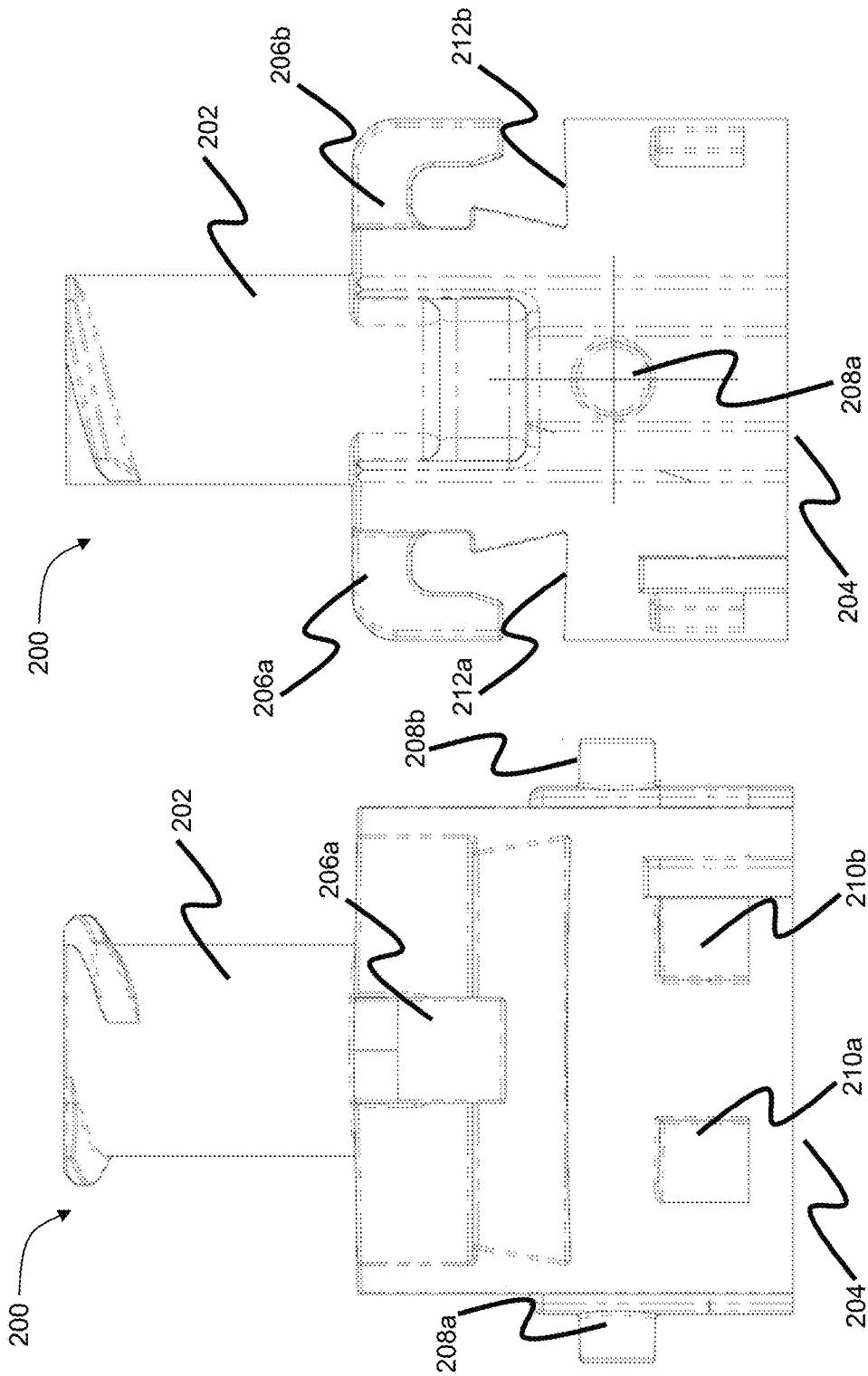
FIG. 3A is an elevation view of a connector of an adapter according to an embodiment.
FIG. 3B is a side view of a connector of an adapter according to an embodiment.
Figure 4:
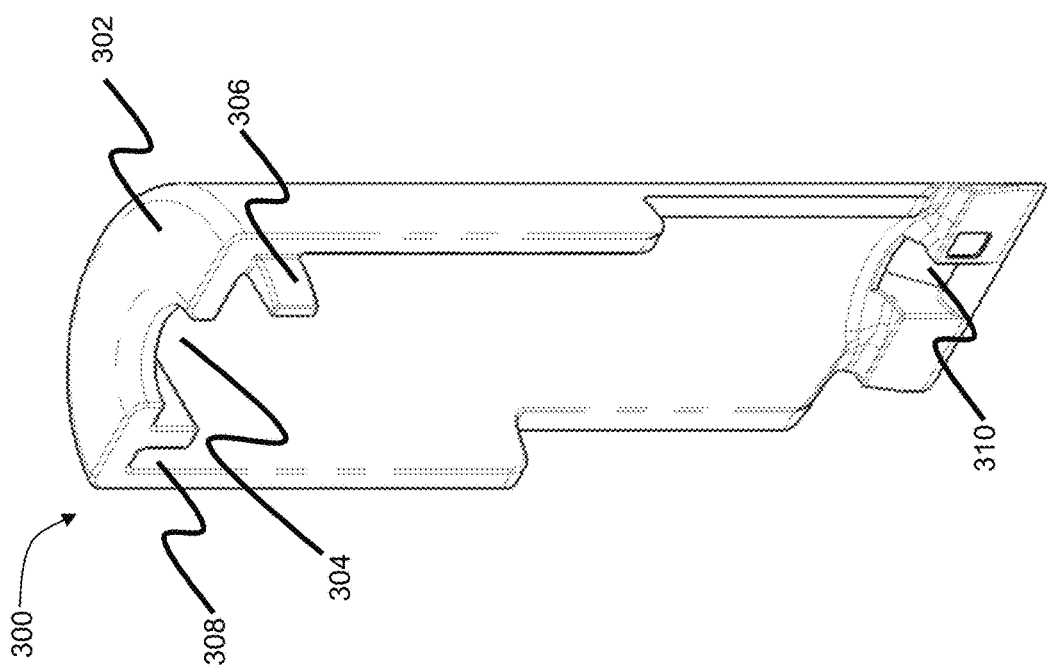
FIG. 4 is a perspective view of a wing of an adapter according to an embodiment.

As can be seen in more detail in FIGS. 2-4, connector 200 can be generally cylindrical, with a diameter of approximately 15 mm and a height of approximately 22 mm in one embodiment. These and other example dimensions given herein are merely examples and can vary in other embodiments according to a type, size, use, application or other characteristic of adapter 100. Connector 200 can be narrowed to the width of fitting 202 at a first end and fitting 204 at a second end. Fittings 202 and 204 can present threading, tapers, pins, or other features to provide more secure connection to desired fitting types.

Connector 200 can present hooks 206a and 206b along the length of the cylinder barrel, situated about 180 degrees around the circumference of connector 200 from each other. Hooks 206a, 206b can define essentially right angles and project outwardly and towards the second end of connector 200.

Connector 200 can also present pins 208a and 208b along the length of the cylinder barrel, situated about 180 degrees around cylinder from each other. Each pin 208a, 208b can be spaced apart by about 90 degrees around the circumference of connector 200 from tabs 206a, 206b. As can be seen in FIG. 3B, pins 208a, 208b project outside of cylinder diameter.

Connector 200 can present locking slots 210a-d (locking slots 210c and 210d not pictured). Locking slots 210 can be depressions in surface of connector 200 projecting inward from cylinder diameter. Locking slots 210 can be primarily rectangular, circular or other shapes. Pairs of locking slots 210 can be arranged around connector 200 about 90 degrees from pins 208.

Connector 200 can present ledges 212a and 212b. Ledges 212a, 212b can be horizontal surfaces arranged on connector 200 to the rear of locking slots 210. Connector 200 can also present guide channels 214a-d (guide channels 214c and 214d not pictured). Guide channels 214 can be semicircular depressions in surface of connector 200 arranged vertically on either side of each pin 208a, 208b.

Referring now to FIG. 4, adapter 100 further comprises at least one wing 300. In one embodiment, two wings 300 are implemented, with a first wing 300 depicted in FIG. 4 and a second wing not depicted. In a two-wing embodiment, each wing 300 essentially defines half of a hollow cylinder bisected lengthwise. The diameter of the wing cylinder can be essentially the same as the diameter of the connector 200. In other embodiments, more wings 300 (e.g., three, with each forming approximately a third of a cylinder, or one forming about half and two each forming about a quarter; or four, with each forming about a fourth of a cylinder or some other configuration; etc.) can be implemented. In the embodiment depicted, wing 300 can have a semi-circular top 302 which is configured to have an opening 304. Opening 304 can be semi-circular or another shape configured such that when wings 300a and 300b are joined to form a complete cylinder, medical tubing or other devices coupled to adapter 100 can pass through and rest in the combined opening. Wing 300 can have tab 306 and slot 308 on inner faces thereof. Tab 306 can protrude out from the open face of wing 300 such that when wings 300a and 300b are joined, tab 306a of wing 300a fits into slot 308b of wing 304b and vice versa. Wing 300 is configured with orifice 310. Orifice 310 is located on an inner surface of wing 300 and has a shape, length and width configured to allow hooks 206a or 206b of connector 200 to slide onto it, rotatably connecting wings 300 to connector 200.

Figure 5:
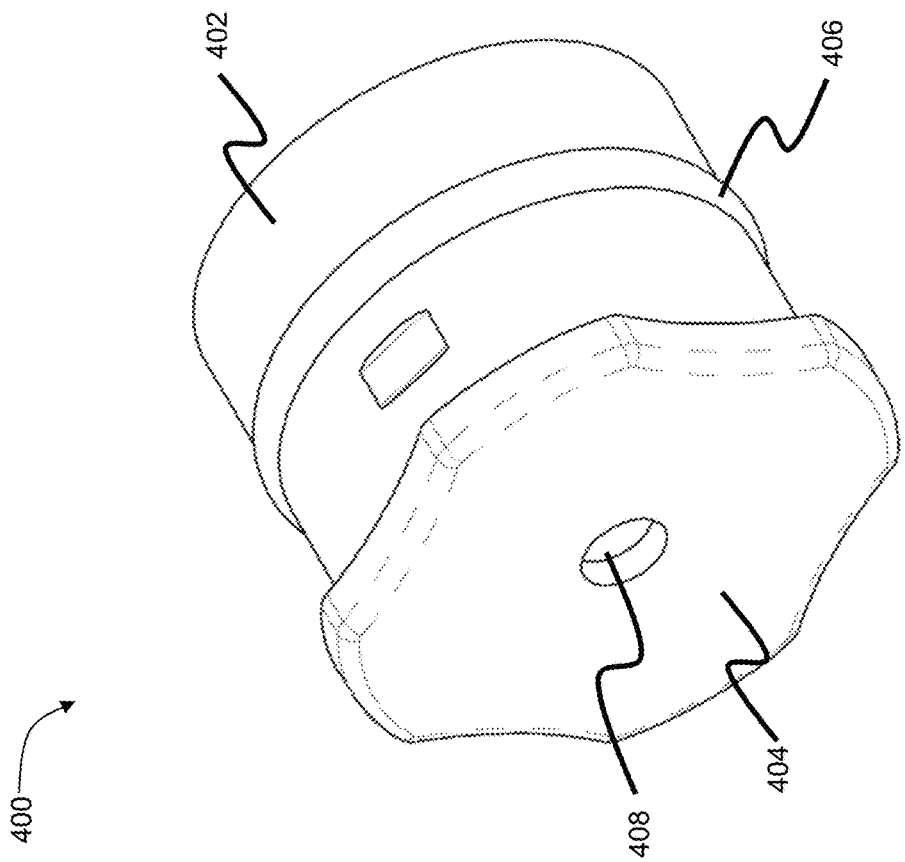
FIG. 5 is a perspective view of a cap of an adapter according to an embodiment.

Referring now to FIG. 5, adapter 100 can further comprise cap 400. Cap 400 comprises sleeve 402 and top 404. Sleeve 402 is hollow, primarily cylindrical, and is configured to insert into fitting 204 of connector 200. Sleeve 402 can present ridge 406, a toroid projection that surrounds the barrel of sleeve 402 and is configured to provide a friction connection when sleeve 402 is inserted into fitting 204. Top 404 can be molded directly onto sleeve 402. Top 402 can be wider than the diameter of sleeve 402 to allow easier removal of cap 400. Top 402 can present aperture 408. As can be seen in FIG. 1, cap 400 can be removably attached to connector 200.

Cap 400 can comprise medical grade plastic, metal, glass, rubber, or other material that can be appropriately sterilized and withstand exposure to medical fluids. Cap 400 can be opaque, translucent or transparent to allow visual inspection of the interior. Cap 400 can be manufactured via molding, 3D printing, or other additive or subtractive manufacturing process.

Figure 6:
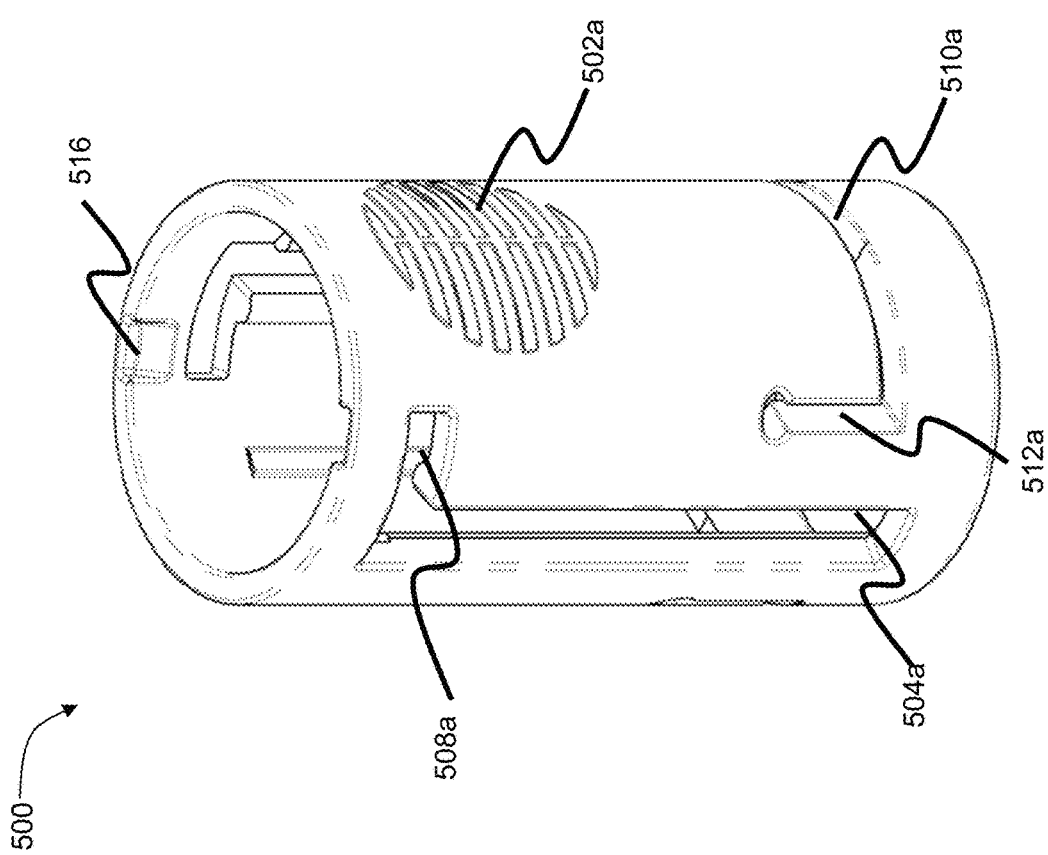
FIG. 6 is a perspective view of a shroud of an adapter according to an embodiment.
Figures 7A, 7B, 7C:
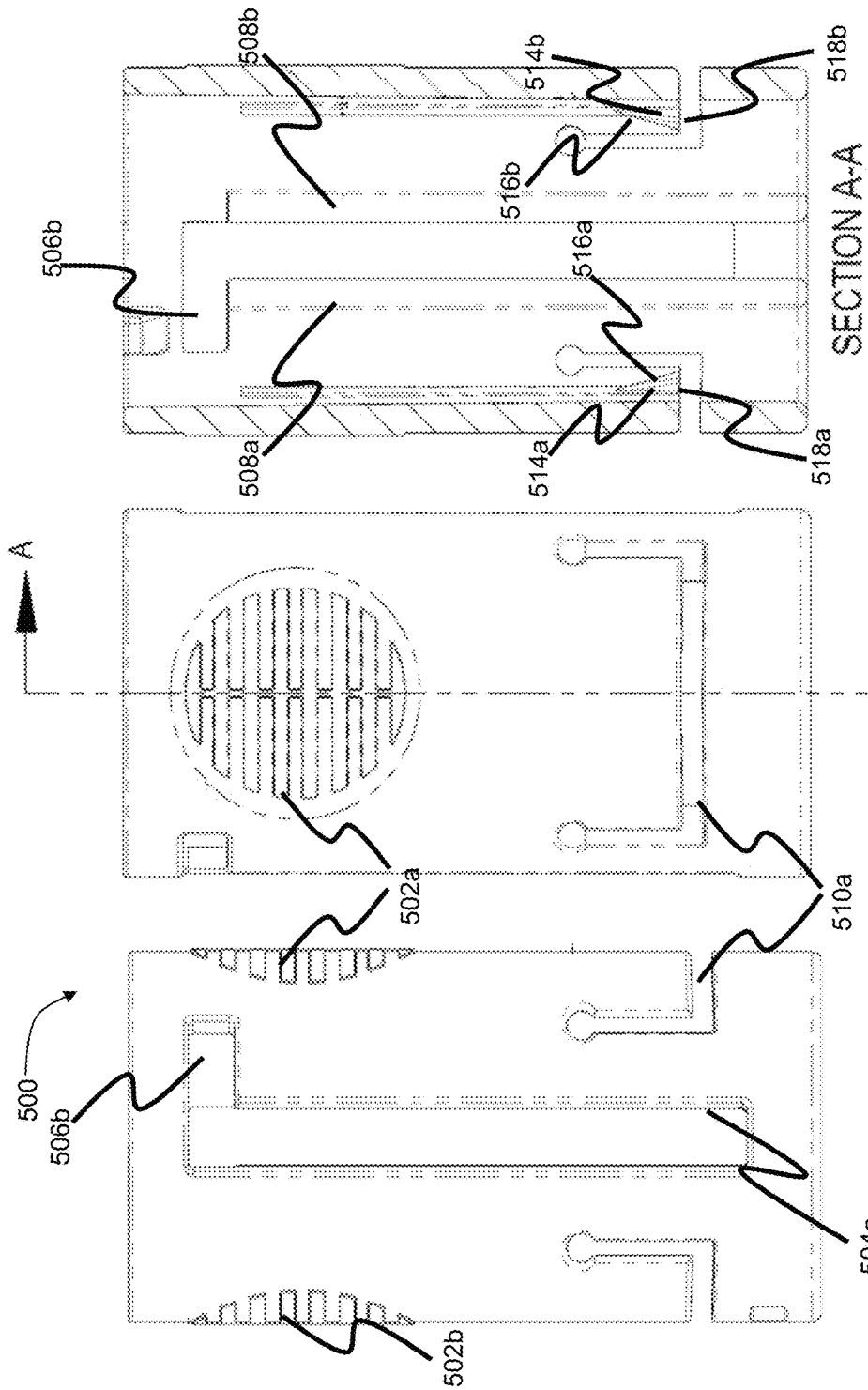
FIG. 7A is an elevation view of a shroud of an adapter according to an embodiment.
FIG. 7B is an elevation view of a shroud of an adapter according to an embodiment.
FIG. 7C is a sectional view of the shroud of FIG. 7B according to an embodiment.

Turning now to FIGS. 6 and 7, adapter 100 further comprises shroud 500. Shroud 500 is generally cylindrical with a first end oriented towards first fitting 202 and a second end oriented towards second fitting 204. The inner diameter of shroud 500 is larger than the diameter of connector 200, but smaller than a diameter defined by pins 208 of connector 200. The length of shroud 500 is at least as long as the length of connector 200.

Shroud 500 can present grips 502a and 502b. Grips 502 can be located along the length of shroud 500. According to one embodiment, grips 502 are raised surfaces incorporated within shroud 500 itself. Grips 502 can also take other forms as necessary to create a more grippable area and allow the easy rotation and movement of shroud 502 relative to connector 200.

Shroud 500 can include longitudinal channels 504a and 504b. In one embodiment, longitudinal channels 504 pass completely through walls of shroud 500, while in other embodiments longitudinal channels 504 can be cut-outs on the inner wall of shroud 500 that do not pass to the exterior. Longitudinal channels 504 can define a line from near a first end of shroud 500 to near the second end of shroud 500. Longitudinal channels 504 can be L-shaped and include transverse portions 506a and 506b toward the first end of shroud 500. Transverse portions 506a, 506b can be approximately perpendicular to longitudinal portions of longitudinal channels 504. Longitudinal channels 504 have a width sufficient to allow pins 208a and 208b to pass through. Longitudinal channels can present vertical guides 508a-d (vertical guides 508a and 508b not shown). Vertical guides 508 can protrude inward from shroud 500 to a depth not exceeding the depth of guide channels 214. Longitudinal channels 504a and 504b can be positioned at about 180 degrees from each other around the wall of shroud 500.

Shroud 500 can include transverse channels 510a and 510b. In one embodiment, transverse channels 510a, 510b can pass completely through the walls of shroud 500, in other embodiments transverse channels 510a, 510b can be cut-outs on the inner wall of shroud 500 that do not pass to the exterior, or cut-outs on the outer wall of shroud 500 that do not pass to the interior. transverse channels 510a, 510b can define a line near the second end of shroud 500. Transverse channels 510a, 510b are positioned such that connector 200 and cap 400 will be enclosed within shroud 500 when second fitting 204 is aligned with transverse channels 510a, 510b. Transverse channels 510a, 510b can be positioned at about 180 degrees from each other around the wall of shroud 500. Transverse channels 510 can include longitudinal portions 512.

Shroud 500 can include locking teeth 514a-d (locking teeth 514c and 514d not shown). Locking teeth 514 can protrude inwardly from inner wall of shroud 500. Locking teeth 514 can define wedge shapes, with tapered facets 516 oriented towards interior of shroud 500 and horizontal forward facets 518 oriented towards the forward end of shroud 500. Locking teeth 514 can be present directly above horizontal channels 510a, 510b between vertical portions 512.

Components of adapter 100 can comprise medical grade plastic, metal, glass, rubber, or other material that can be appropriately sterilized and withstand exposure to medical fluids. Components of adapter 100 can be manufactured via molding, 3D printing, or other additive or subtractive manufacturing processes, in various embodiments.

Figure 8:
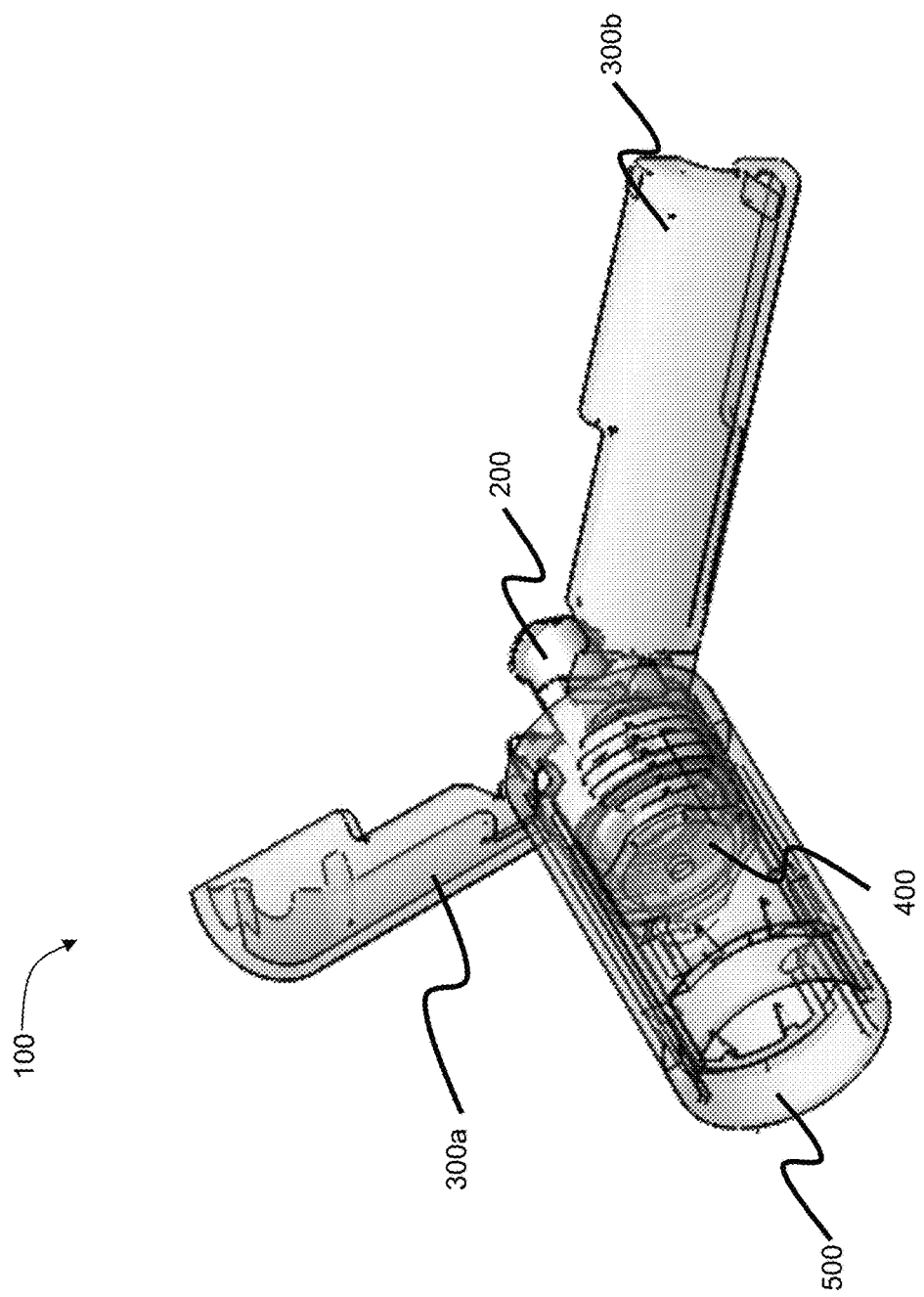
FIG. 8 is a perspective view of an assembled adapter according to an embodiment.

In use and operation, adapter 100 can have three modes: open, partially locked, and locked. As can be seen in FIG. 8, in open mode wings 300 are rotatably attached at orifices 310 to hooks 206 of connector 200. Cap 400 is removably coupled to second fitting 204 of connector 200. Connector 200 is arranged in the top of shroud 500 such that second fitting 204 is disposed within shroud 500, pins 208a, 208b are disposed within horizontal portions 508a, 508b of longitudinal channels 504a, 504b, and top fitting 202 is exposed.

As can be seen in FIG. 9, tubing 600 comprising a tubing connector 610 (for example, an infusion line with a male Luer connector on an end proximate adapter 100) can be coupled to top fitting 202. Tubing connector 610 and connector 200 can be rotated (relative to shroud 500) such that pins 208a, 208b are aligned with the vertical portions of longitudinal channels 504a, 504b. In the pictured embodiment, longitudinal channels 504a, 504b are configured such that clockwise rotation is allowed, however other embodiments could include counterclockwise rotation. As seen in FIG. 10, wings 300a, 300b can be pivoted, at hooks 206a, 206b to form a cylinder substantially enclosing tubing connector 610 and a partial length of tubing 600.

FIGS. 10-12 depict insertion of connector 200 into shroud 500 by moving connector 200 towards second end of shroud 500. As used herein, forward movement is movement towards second end of shroud 500, whereas backward movement is movement toward first end of shroud 500. As seen in FIG. 10, alignment of pins 208a, 208b with longitudinal channels 504a, 504b allows movement of connector 200, wings 300, tubing connector 610, and cap 400 forward into shroud 500. Backward movement is also possible in this open mode. Rotation of connector 200 is restricted by interaction of pins 208a, 208b with longitudinal channels 504a, 504b and guide channels 214a, 214b, 214c, 214d with vertical guides 508a, 508b, 508c, 508d. Adapter 100 remains in open mode until connector 200 has advanced into shroud 500 such that forward edges of locking slots 210 pass beyond forward facets 518 of locking teeth 514, causing adapter 100 to enter partially locked mode.

As seen in FIG. 11, in partially locked mode, locking teeth 514 prevent backward movement of connector 200, while tapered facets 516 (not shown) allow continued forward movement. In partially locked mode, both first fitting 202 and second fitting 204 are inaccessible. First fitting 202 (and tubing connector 610 coupled therewith) is inaccessible because it is enclosed within closed wings 300a, 300b, which are prevented from opening by being partially enclosed within shroud 500. Second fitting 204 is inaccessible because it is covered by cap 400, which is enclosed within shroud 500. Partially locked mode provides a state in which tubing 600 is irremovably connected to adapter 100, while still preventing access to second fitting 204.

As seen in FIG. 12, access to second fitting 204 is only permitted in a locked mode. From partially locked mode, connector 200 can be moved forward until pins 208 encounter forward edges of longitudinal channels 504, and ledge 212 passes beyond forward facets 518 of locking teeth 514. In this locked mode, cap 400 is exposed from shroud 500 and can be selectively removed by a user, at least partially exposing second fitting 204. This at least partial exposure of second fitting 204 is sufficient to enable a second coupling, such as one coupled to another length of medical tubing, to be coupled to second fitting 204. Connector 200 is prevented from further forward movement by interaction of pins 208 with forward edge of longitudinal channels 504. Connector 200 is also prevented from backward movement by interaction of locking teeth 514 with ledges 212 of connector 200. First fitting 202 and tubing connector 610 remain inaccessible because of enclosure within closed wings 300a, 300b and shroud 500. Fluid communication is established between the first coupling coupled to first fitting 202 and second coupling coupled to second fitting 204.

Figure 13:
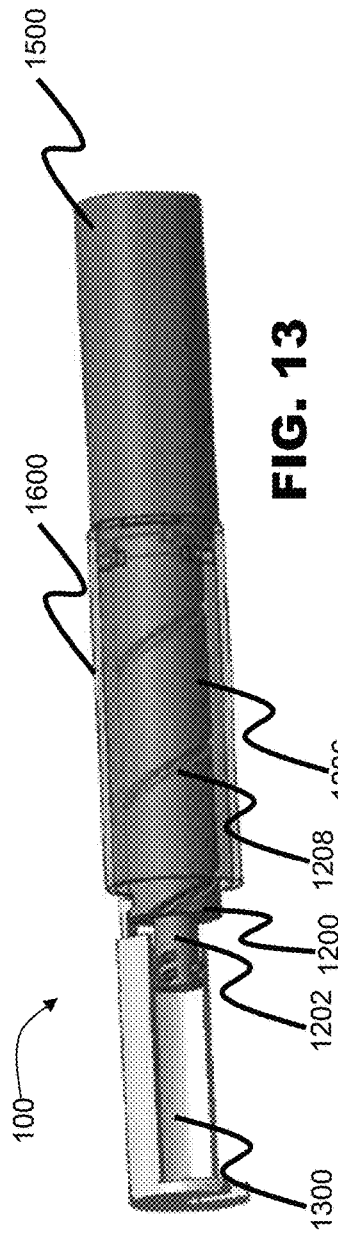
FIG. 13 is a perspective view of an adapter in an open mode according to an embodiment.
Figure 14:
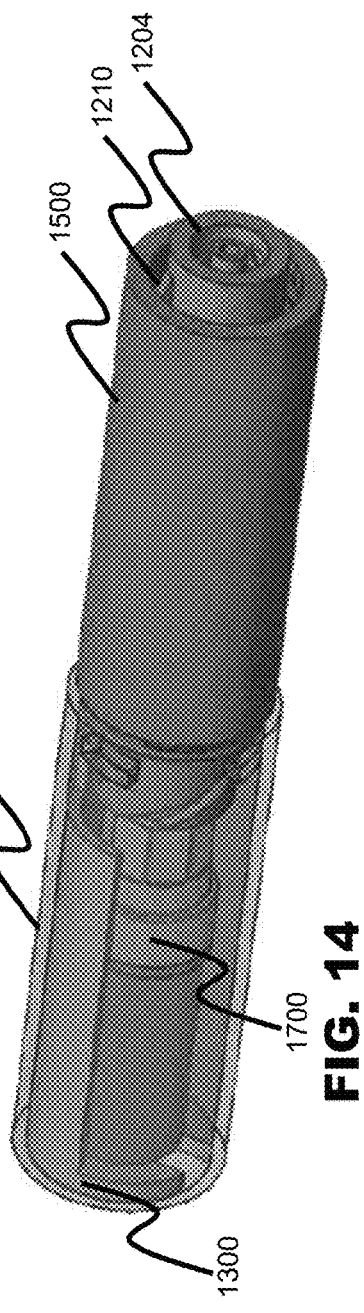
FIG. 14 is a perspective view of an adapter in a locked mode according to an embodiment.
Figure 15:
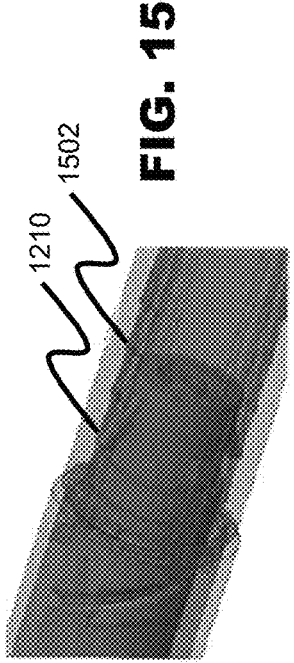
FIG. 15 is a perspective view of an adapter in a partially locked mode according to an embodiment.

An alternative embodiment is shown in FIGS. 13-15. As is depicted in FIG. 13, adapter 1000 comprises connector 1200, wing 1300, inner shroud 1500 and outer shroud 1600. Adapter 1000 provides a tamper-proof connection similar to adapter 100; however, adapter 1000 uses a twisting mechanism to move the connector into a locked position.

Connector 1200 can present first fitting 1202 and second fitting 1204, which can be substantially similar to first fitting 202 and second fitting 1204 described above. Connector 1200 also presents shaft 1206. Shaft 1206 can include shaft threading 108 which comprises a spiral depression around exterior of shaft 1206. Shaft 1206 can be at least as long as inner shroud 1500 discussed below. As can be seen in FIGS. 14 and 15, shaft 1206 can also present a plurality of shaft teeth 1210. Shaft teeth 1210 can be wedge shaped, with a narrow end oriented towards the forward end of shaft 1206 and a flat rear facet oriented towards the rear end of shaft 1206. Adapter 1000 further comprises wing 1300. Wing 300 essentially defines half of a hollow cylinder bisected lengthwise. The diameter of the wing cylinder can be essentially the same as the diameter of the connector 1200. Wing 1300 can have a circular top 302 which is configured to have an opening 304. Opening 304 can be semi-circular or another shape configured such that medical tubing can rest within it. Wing 1300 can be rotatably connected to connector 1200 via a hook or other hinging mechanism. Wing 1300 can comprise similar materials and can be manufactured via similar methods to wing 300.

Adapter 1000 further comprises inner shroud 1500. Inner shroud 1500 can define a cylinder with inner diameter sufficient to allow entry of connector 1200 and length sufficient to allow first fitting 1202 and second fitting 1204 to be exposed. As can be seen in FIG. 15, inner shroud 1500 can comprise locking teeth 1502. Locking teeth 1502 can be wedge shaped, with wide facets oriented towards the rear of inner shroud 1500. Locking teeth 1502 can be positioned to interact with shaft teeth 1210. Inner shroud 1500 can also present threading (not shown) adapted to interact with shaft threading 1208. Inner shroud 1500 can also comprise grips (not shown) similar to grips 502a, 502b.

Adapter 1000 further comprises outer shroud 1600. Outer shroud 1600 can define a cylinder with inner diameter sufficient to allow entry of inner shroud 1500 and length sufficient to encompass wing 1300. Outer shroud 1500 can also comprise grips (not shown) similar to grips 502a, 502b.

Components of adapter 1000 can comprise similar materials and can be manufactured via similar methods as adapter 100.

In use and operation, adapter 1000 is operable in three modes: open, partially locked, and locked. As can be seen in FIG. 13, in open mode, first fitting 1202 can be exposed to allow tubing 1700 to be connected. Wing 1300 can hinge over tubing 1700 to provide protection and hold tubing 1700 in place. As used herein, forward movement is movement towards second end of inner shroud 1500, whereas backward movement is movement toward first end of inner shroud 1500.

After tubing 1700 has been attached, the user can rotate wing 1300, connector 1200 and tubing 1700 relative to inner shroud 1500. Shaft threading 1208 can interact with threading within shroud to guide the forward rotational movement. As shown in FIG. 15, as connector 1200 moves forward relative to inner shroud 1500, shaft teeth 1210 slide can past locking teeth 1502 in several steps. The interaction of shaft teeth 1210 and locking teeth 1502 prevent backward movement of connector 1200 beyond the previous step. When connector 1200 has advanced forward such that wing 1300 cannot open, adapter 100 is in a partially locked mode, in which neither first fitting 1202 nor second fitting 1204 are accessible.

Connector 1200 can continue to be rotated forward until fitting 1204 is revealed in a fully locked mode (as can be seen in FIG. 14).

Referring to FIG. 16, still another embodiment of an adapter 1800 can comprise a lock-out cap. Adapter 1800 can provide a deterrent to or prevent incorrect use of a Luer to non-Luer, or other type of, adapter. Adapter 1800 can comprise shroud 1810, first cap connector 1820, and second cap connector 1830. First cap connector 1820 can present first cap fitting 1822. Second cap connector 1820 can present second cap fitting (not visible in FIG. 16) and pin 1834. Pin 1834 can be configured to interact with channel 1812 of shroud 1810.

In operation, as an external fitting is coupled to first cap fitting 1822 and rotatably secured thereto with a sufficient amount of torque, first cap connector 1820 and second cap connector 1830 will rotate relative to shroud 1810, causing pin 1834 to slide within channel 1812 of shroud 1810 and second cap connector 1830 to then slide within shroud 1810 from the body of adapter 1800, thereby enabling shroud 1810 to be removed to expose the second cap fitting. Such a lock-out cap can be implemented with other embodiments depicted and discussed herein, or in still further embodiments contemplated herein.

Adapters 100, 1000, 1800 of the present disclosure and other embodiments thereof provide a number of benefits. Because second fittings can be different from first fittings, the adapters allow interconnection of diverse connectors and fitting types. Adapters 100, 1000 also provide a permanent, tamper-proof connection to medical tubing, ensuring that medical tubing can only be connected to fittings that are compatible with second fittings. In one embodiment, this can mean that tubing with a Luer style fitting can be permanently adapted to present a 80369-6 neuraxial connector, eliminating potential wrong-route administration errors. The partially-locked mode of adapters 100, 1000 further provides the benefit of a permanent connection to medical tubing, while preventing access to the second fittings. This provides indication that adapters 100, 1000 and the attached tubing have not been used since the attachment.

While embodiments depicted and discussed herein relate generally to medical applications, in particular medical tubing, these and other embodiments are not limited to these applications or examples. In some embodiments, adapter 100 can be used in other medical applications, such as to couple cables, wires, leads, hoses, pipes, or other devices other than tubing. In still other embodiments, adapter 100 can be used in non-medical applications, including veterinary, industrial, electronics, automation, plumbing, gas, automotive, aviation or other still other applications in which it may be desired to couple tubing, cables, wires, hoses, pipes, leads or other devices, including in secure and tamper-proof situations. Thus, a wide variety of uses and applications are contemplated and can be implemented in accordance with embodiments.

Various embodiments of devices, systems and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An adapter for adapting a first coupling to one of a plurality of second couplings, the adapter comprising:
   a connector comprising a first fitting arranged at a first end of the connector and a second fitting arranged at a second end of the connector, the first fitting configured to accept the first coupling and the second fitting configured to accept said one of a plurality of second couplings, said one of a plurality of second couplings being different from the first coupling;
   a shroud having a first end and a second end; and
   at least one wing moveably connected to the connector and configured to be closeable around the first fitting and the first coupling such that the wing and the connector can be moved within the shroud from the first end of the shroud toward the second end of the shroud such that the shroud can be moved from an unlocked position where the second fitting and said one of a plurality of second couplings are substantially enclosed within the shroud to a locked position in which the first fitting and the first coupling are substantially enclosed within the shroud and the second fitting is at least partially exposed at the second end of the shroud; such that in the unlocked position, the second fitting is inaccessible; and in the locked position, the first fitting is inaccessible; whereby in the unlocked position, the adapter is accessible only to the first coupling; and in the locked position, the adapter is accessible only to said one of a plurality of second couplings.

2. The adapter of claim 1, wherein the first coupling and said one of a plurality of second couplings are different in respect to at least one characteristic selected from the group consisting of: size, shape, type and gender.

3. The adapter of claim 1, wherein the first fitting is one of a male or a female fitting and the second fitting is the other of the female or the male fitting.

4. The adapter of claim 3, wherein the first fitting is a female Luer fitting and the second fitting is a male 80369-6 connector.

5. The adapter of claim 1, wherein one of the first fitting or the second fitting comprises a Luer fitting and the other of the first fitting or the second fitting comprises an 80369-6 connector.

6. The adapter of claim 1, further comprising a cap configured to be removably coupled to the second fitting, wherein the cap can be selectively removed from the second fitting only when the connector is in the locked position.

7. The adapter of claim 1, wherein the at least one wing comprises two wings moveably connected to the connector and configured to form a cylinder that closes around the first fitting and the first coupling.

8. The adapter of claim 1, wherein the shroud further comprises external grips.

9. The adapter of claim 1, wherein the connector further comprises at least one ledge and at least one pin and the shroud comprises at least one longitudinal channel and at least one locking tooth, and further wherein when the connector is in the locked position, movement toward the first end of the shroud is prevented by projection of the at least one locking tooth into the at least one ledge and movement toward the second end of the shroud is prevented by projection of the at least one pin into the at least one longitudinal channel.

10. The adapter of claim 1, further configured to enter an intermediary locked position in which the connector and the at least one wing are moved within the shroud to a position between the first end of the shroud and the locked position, wherein the first fitting and the second fitting are enclosed within the shroud and the connector is prevented from movement toward the first end of the shroud in the intermediary locked position.

11. The adapter of claim 10, wherein the connector further comprises at least one locking slot, and further wherein when the connector is in the intermediary locked position, movement toward the first end of the shroud is prevented by projection of at least one locking tooth into the at least one locking slot.

12. The adapter of claim 1, wherein the first coupling is coupled to a first medical tubing and said one of a plurality of second couplings is coupled to a second medical tubing, and wherein fluid communication between the first medical tubing and the second medical tubing is established when the first coupling is coupled to the first fitting, the locked position is established, and said one of a plurality of second couplings is coupled to the second fitting.

13. An adapter for adapting a first coupling to one of a plurality of second couplings, the adapter comprising:
   a connector comprising a first fitting arranged at a first end of the connector and a second fitting arranged at a second end of the connector, the first fitting configured to accept the first coupling and the second fitting configured to accept said one of a plurality of second couplings;
   a shroud having a first end and a second end; and
   a first wing and a second wing each moveably connected to the connector and configured to form a cylinder substantially enclosing the first fitting and the first coupling such that the cylinder and the connector can be moved within the shroud from the first end of the shroud toward the second end of the shroud such that the shroud can be moved from an unlocked position where the second fitting and said one of a plurality of second couplings are substantially enclosed within the shroud to a locked position in which the first fitting is enclosed within the shroud and the second fitting is at least partially exposed at the second end of the shroud; such that in the unlocked position, the second fitting is inaccessible; and in the locked position, the first fitting is inaccessible; whereby in the unlocked position, the adapter is accessible only to the first coupling; and in the locked position, the adapter is accessible only to said one of a plurality of second couplings.

14. A method of adapting a first coupling to one of a plurality of second couplings, the method comprising:
   providing a connector comprising a first fitting at a first end of the connector and a second fitting at a second end of the connector, the first fitting configured to accept the first coupling and the second fitting configured to accept said one of a plurality of second couplings;
   moveably coupling a first wing and a second wing to the connector such that the first and second wings can be selectively moved together to form a cylinder substantially enclosing the first fitting and the first coupling; and slidably coupling a shroud having a first end and a second end to the connector such that the second fitting is arranged substantially within the shroud, and the cylinder and the connector can be slid together within the shroud from a first end of the shroud toward the second end of the shroud such that the shroud can be moved from an unlocked position where the second fitting and second coupling are substantially enclosed within the shroud to a locked position in which the first fitting and the first coupling are substantially enclosed within the cylinder and the shroud and the second fitting is substantially exposed at the second end of the shroud; such that in the unlocked position, the second fitting is inaccessible; and in the locked position, the first fitting is inaccessible; whereby in the unlocked position, the adapter is accessible only to the first coupling; and in the locked position, the adapter is accessible only to said one of a plurality of second couplings.

15. An adapter for adapting a first coupling to one of a plurality of second couplings, the adapter comprising:
   a connector comprising a first fitting and a second fitting configured to accept the first coupling and said one of a plurality of second couplings, respectively, the first fitting being at a first end of the connector and the second fitting being at a second end of the connector;
   one or more wings coupled to the connector and configured to be closeable to form a cylinder around the first fitting and the first coupling;
   a first shroud having a first end and a second end and an inner diameter sized to allow the connector and the cylinder to slide and rotate therewithin; and
   a second shroud having a first end and a second end, wherein the second end is coupled at the first end to the second end of the first shroud and having an inner diameter sized to allow the connector to slide and rotate therewithin, such that as the cylinder is advanced from the first end of the first shroud toward the second end of the first shroud, the connector rotates within the second shroud and moves toward the second end of the second shroud such that the second shroud can be moved from an unlocked position where the second fitting and said one of a plurality of second couplings are substantially enclosed within the second shroud to a locked position in which the connector is prevented from movement toward the first end of the first shroud, the first fitting is enclosed within the first shroud, and the second fitting is at least partially exposed at the second end of the the second shroud; such that in the unlocked position, the second fitting is inaccessible; and in the locked position, the first fitting is inaccessible; whereby in the unlocked position, the adapter is accessible only to the first coupling; and in the locked position, the adapter is accessible only to said one of a plurality of second couplings.

16. The adapter of claim 15, wherein the connector further comprises a first spiral threading configured to interact with a corresponding second spiral threading on an inner surface of the second shroud.

* * * * *